(12) United States Patent
Robertson

(10) Patent No.: US 11,723,936 B2
(45) Date of Patent: Aug. 15, 2023

(54) **THERAPEUTIC USES OF *LACTOBACILLUS PLANTARUM***

(71) Applicant: Probi AB, Lund (SE)

(72) Inventor: Anna-Karin Robertson, Lund (SE)

(73) Assignee: Probi AB, Lund (SE)

( * ) Notice: Subject to any disclaimer, the term of this patent is extended or adjusted under 35 U.S.C. 154(b) by 6 days.

(21) Appl. No.: 16/623,829

(22) PCT Filed: Jun. 18, 2018

(86) PCT No.: PCT/EP2018/066152
§ 371 (c)(1),
(2) Date: Dec. 18, 2019

(87) PCT Pub. No.: WO2018/234255
PCT Pub. Date: Dec. 27, 2018

(65) Prior Publication Data
US 2021/0138004 A1 May 13, 2021

(30) Foreign Application Priority Data
Jun. 19, 2017 (GB) ...................... 1709763

(51) Int. Cl.
| | |
|---|---|
| *A61K 35/747* | (2015.01) |
| *A23K 10/18* | (2016.01) |
| *A23L 33/135* | (2016.01) |
| *A61P 1/00* | (2006.01) |
| *A61K 9/00* | (2006.01) |

(52) U.S. Cl.
CPC ............ *A61K 35/747* (2013.01); *A23K 10/18* (2016.05); *A23L 33/135* (2016.08); *A61K 9/0053* (2013.01); *A61P 1/00* (2018.01); *A23V 2002/00* (2013.01); *A23Y 2220/67* (2013.01)

(58) Field of Classification Search
CPC ...... A61P 1/00; A23L 33/135; A23Y 2220/67; A61K 35/747; A61K 9/0053; A23K 10/18; A23V 2002/00
See application file for complete search history.

(56) References Cited

U.S. PATENT DOCUMENTS

2012/0238468 A1  9/2012  Tuk et al.

FOREIGN PATENT DOCUMENTS

| EP | 1769801 A1 | 4/2007 |
|---|---|---|
| EP | 2136825 A2 | 12/2009 |

(Continued)

OTHER PUBLICATIONS

Gophna et al., (Environmental Microbiology. Dec. 2016. 19(3). (Year: 2016).*

(Continued)

*Primary Examiner* — Jana A Hines
(74) *Attorney, Agent, or Firm* — McCarter & English, LLP; Yu Lu

(57) ABSTRACT

The invention relates to the use of at least one strain of *Lactobacillus plantarum* in a method for increasing the numbers of *Oscillospira* spp. in a subject and preferably maintaining the increased numbers, the method comprising administering the at least one strain of *Lactobacillus plantarum* to the subject. Preferably, the uses and methods of the invention are used to treat a subject with dysbiosis of *Oscillospira* spp., especially those suffering from an associated disorder, syndrome or disease.

Figure 1:
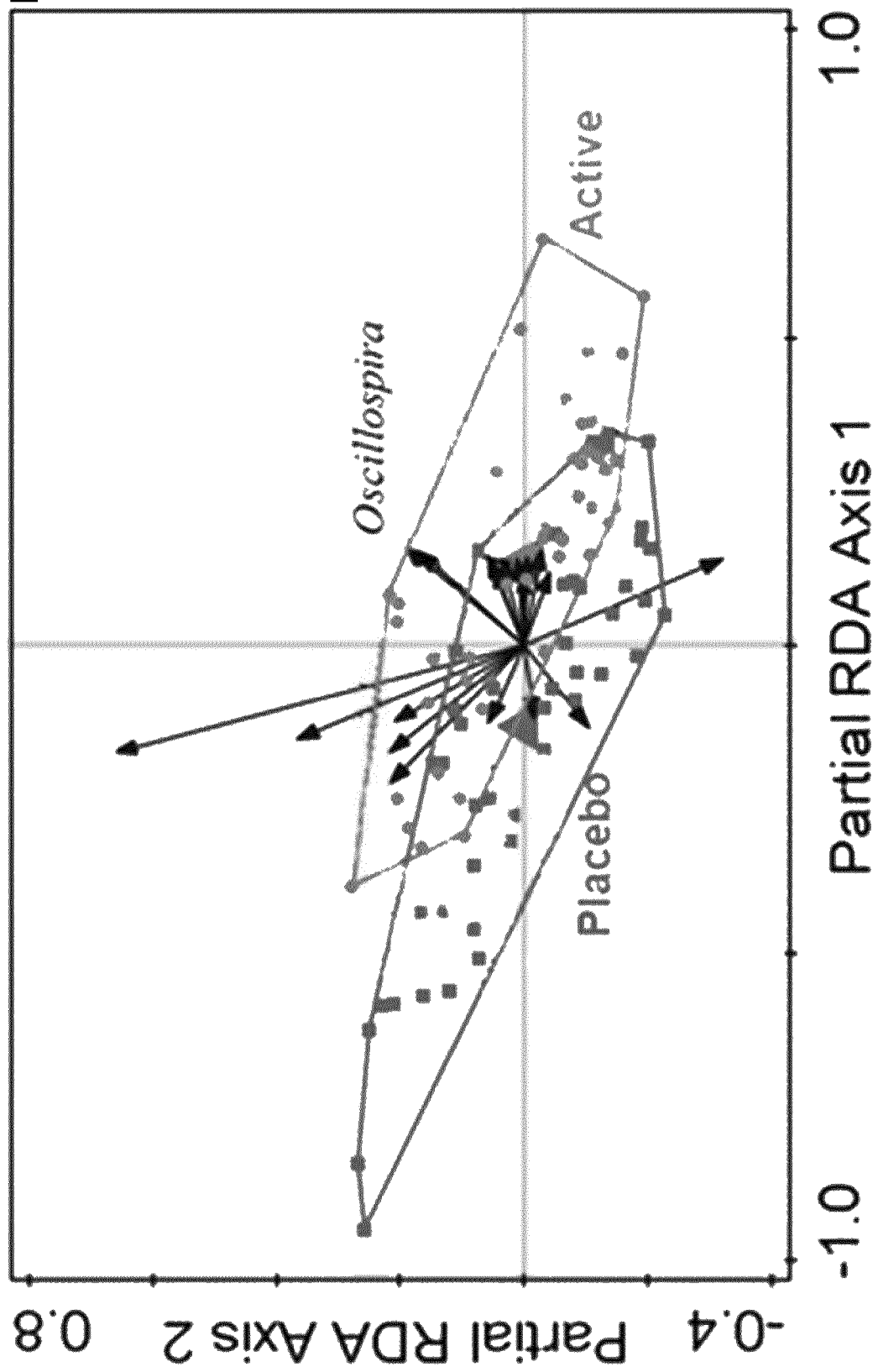

13 Claims, 3 Drawing Sheets
Specification includes a Sequence Listing.

(56) References Cited

FOREIGN PATENT DOCUMENTS

| WO | 1999/07827 A1 | 2/1999 | |
|----|---------------|--------|---|
| WO | 2007/036230 A1 | 4/2007 | |
| WO | 2007/040444 A1 | 4/2007 | |
| WO | WO-2007040444 A1 * | 4/2007 | ............ A23L 29/065 |
| WO | 2008/105715 A2 | 9/2008 | |
| WO | WO-2008105715 A2 * | 9/2008 | ................ A61P 1/14 |
| WO | 2016/149687 A1 | 9/2016 | |
| WO | 2016/165555 A1 | 10/2016 | |

OTHER PUBLICATIONS

Haro et al., (The Journal of Clinical Endocrinology & Metabolism, vol. 101, Issue 1, Jan. 1, 2016, pp. 233-242) (Year: 2016).*
Romagnolo et al., (Nutrition Today. 2017. vol. 52, No. 5 pp. 208-222) (Year: 2017).*
Arpaia et al., Metabolites produced by commensal bacteria promote peripheral regulatory T-cell generation. Nature. Dec. 19, 2013;504(7480):451-5.
Brahe et al., Is butyrate the link between diet, intestinal microbiota and obesity-related metabolic diseases? Obes Rev. Dec. 2013;14(12):950-9.
Canani et al., Potential beneficial effects of butyrate in intestinal and extraintestinal diseases World J Gastroenterol. Mar. 28, 2011;17(12):1519-28.
Chan et al., High fat diet induced atherosclerosis is accompanied with low colonic bacterial diversity and altered abundances that correlates with plaque size, plasma A-FABP and cholesterol: a pilot study of high fat diet and its intervention with Lactobacillus rhamnosus GG (LGG) or telmisartan in ApoE(-/-) mice. BMC Microbiol. Nov. 8, 2016;16(1):264. 13 pages.
Chang et al., The microbial metabolite butyrate regulates intestinal macrophage function via histone deacetylase inhibition. Proc Natl Acad Sci U S A. Feb. 11, 2014;111(6):2247-52.
Daniells, What is a probiotic? IPA releases guidance document on qualifying probiotics. NUTRA ingredients-usa.com. Retrieved online at: https://www.nutraingredients-usa.com/Article/2017/06/05/What-is-a-probiotic-IPA-releases-guidance-document-on-qualifying-probiotics. 4 pages. Jun. 5, 2017.
De Angelis et al., Fecal microbiota and metabolome of children with autism and pervasive developmental disorder not otherwise specified. PLoS One. Oct. 9, 2013;8(10):e76993 18 pages.
Ducrotte et al., Clinical trial: Lactobacillus plantarum 299v (DSM 9843) improves symptoms of irritable bowel syndrome. World J Gastroenterol. Aug. 14, 2012;18(30):4012-8.
Endo et al., Butyrate-producing probiotics reduce nonalcoholic fatty liver disease progression in rats: new insight into the probiotics for the gut-liver axis. PLoS One. May 16, 2013;8(5):e63388. 19 pages.
European Medicines Agency, Guideline on the evaluation of medicinal products for the treatment of irritable bowel syndrome. CPMP/EWP/785/97 Rev. 1, 18 pages, Sep. 25, 2014.
Gophna et al., Oscillospira and related bacteria—From metagenomic species to metabolic features. Environ Microbiol. Mar. 2017;19(3):835-841.
Hamilton et al., Changes in intestinal barrier function and gut microbiota in high-fat diet-fed rats are dynamic and region dependent. Am J Physiol Gastrointest Liver Physiol. May 15, 2015;308(10):G840-51.
Ipa, Evaluation of the State of Science Outside of Conventional Probiotic Usage Paper #1: Probiotics and Metabolic Syndrome. International Probiotics Association. Retrieved online at: http://www.nutraingredients-usa.com. 3 pages, Dec. 5, 2016.
Ipa, Evaluation of the State of Science Outside of Conventional Probiotic Usage. Paper #1: Probiotics and Metabolic Syndrome. International Probiotics Association. 4 pages. (2015).
Ipa, Guidelines, Are Probiotics Safe? International Probiotics Association. Retrieved online at: http://internationalprobiotics.org/resources/guidelines/ 6 pages, Aug. 11, 2016.
Ipa, IPA guidelines to qualify a microorganism to be termed as 'probiotic.' International Probiotics Association. 5 pages.
Ipa, Paper #2: Inflammatory Conditions. International Probiotics Association. Retrieved online at: https://www.nutraingredients-usa.com/News/Promotional-Features/Paper-2-Inflammatory-Conditions. 2 pages, May 1, 2017.
Kaakoush et al., icrobial dysbiosis in pediatric patients with Crohn's disease. J Clin Microbiol. Oct. 2012;50(10):3258-66.
Karlsson et al., Gut metagenome in European women with normal, impaired and diabetic glucose control. Nature. Jun. 6, 2013;498(7452):99-103.
Karlsson et al., Probiotic therapy to men with incipient arteriosclerosis initiates increased bacterial diversity in colon: a randomized controlled trial Atherosclerosis. Jan. 2010;208(1):228-33.
Klindworth et al., Evaluation of general 16S ribosomal RNA gene PCR primers for classical and next-generation sequencing-based diversity studies. Nucleic Acids Res. Jan. 7, 2013;41(1):e1. 11 pages.
Lam et al., Increased gut permeability and microbiota change associate with mesenteric fat inflammation and metabolic dysfunction in diet-induced obese mice. PLoS One. 2012;7(3):e34233. 10 pages.
Leps et al., Multivariate Analysis of Ecological Data using CANOCO. Cambridge University Press, Cambridge. 283 pages, (2003).
Mackie et al., Ecology of uncultivated Oscillospira species in the rumen of cattle, sheep, and reindeer as assessed by microscopy and molecular approaches. Appl Environ Microbiol. Nov. 2003;69(11):6808-15.
Manichanh et al., Anal gas evacuation and colonic microbiota in patients with flatulence: effect of diet. Gut. Mar. 2014;63(3):401-8.
Molin, Probiotics in foods not containing milk or milk constituents, with special reference to Lactobacillus plantarum 299v. Am J Clin Nutr. Feb. 2001;73(2 Suppl):380S-385S.
Niedzielin et al., A controlled, double-blind, randomized study on the efficacy of Lactobacillus plantarum 299V in patients with irritable bowel syndrome. Eur J Gastroenterol Hepatol. Oct. 2001;13(10):1143-7.
Nobaek et al., Alteration of intestinal microflora is associated with reduction in abdominal bloating and pain in patients with irritable bowel syndrome. Am J Gastroenterol. May 2000;95(5):1231-8.
Pan et al., Changes in gastric microbiota induced by Helicobacter pylori infection and preventive effects of Lactobacillus plantarum ZDY 2013 against such infection. J Dairy Sci. Feb. 2016;99(2):970-981.
Qin et al., A metagenome-wide association study of gut microbiota in type 2 diabetes. Nature. Oct. 4, 2012;490(7418):55-60.
Seo et al., Clostridium Butyricum MIYAIRI 588 Improves High-Fat Diet-Induced Non-Alcoholic Fatty Liver Disease in Rats. Dig Dis Sci. 2013;58:3534-44.
Singh et al., Activation of Gpr109a, receptor for niacin and the commensal metabolite butyrate, suppresses colonic inflammation and carcinogenesis Immunity. Jan. 16, 2014;40(1):128-39.
The Human Microbiome Project Consortium, Structure, function and diversity of the healthy human microbiome. Nature. Jun. 13, 2012;486(7402):207-14.
Tibshirani et al., Diagnosis of multiple cancer types by shrunken centroids of gene expression. Proc Natl Acad Sci U S A. May 14, 2002;99(10):6567-72.
Tims et al., Microbiota conservation and BMI signatures in adult monozygotic twins. ISME J. Apr. 2013;7(4):707-17.
Tun et al., Exposure to household furry pets influences the gut microbiota of infant at 3-4 months following various birth scenarios. Microbiome. Apr. 6, 2017;5(1):40. 14 pages.
Tusher et al., Significance analysis of microarrays applied to the ionizing radiation response. Proc Natl Acad Sci U S A. Apr. 24, 2001;98(9):5116-21.
Vrieze et al., Transfer of intestinal microbiota from lean donors increases insulin sensitivity in individuals with metabolic syndrome. Gastroenterology. Oct. 2012;143(4):913-6.
Yadav et al., Beneficial metabolic effects of a probiotic via butyrate-induced GLP-1 hormone secretion. J Biol Chem. Aug. 30, 2013;288(35):25088-97.

(56) References Cited

OTHER PUBLICATIONS

Yang et al., The gut microbiota: a key regulator of metabolic diseases. BMB Rep. Oct. 2016;49(10):536-541.
Kharkevich. Pharmacology., 10th ed. GEOTAR-Media, 2010;73-74.
Konikoff et al., Oscillospira: a Central, Enigmatic Component of the Human Gut Microbiota. Trends Microbiol. Jul. 2016;24(7):523-524.
Zhulenko et al., Pharmacology. 2008;34-35.
Miao et al., Erythrocyte n-6 Polyunsaturated Fatty Acids, Gut Microbiota and Incident Type 2 Diabetes: A Prospective Cohort Study. Curr Dev Nutr. Jun. 2020;4(Suppl. 1):1452, 2 pages.
Solch et al., Differing Associations Between the Most Abundant Genera of the Fecal Microbiome and Sex, Fiber Intake Score, Stress, Stool Consistency and BMI in Healthy Young Adults. Curr Dev Nutr. Jun. 2020;4(Suppl. 2):1586, 2 pages.
Taniguchi et al., Effects of short-term endurance exercise on gut microbiota in elderly men. Physiol Rep. 2018;6(23):e13935, 25 pages.

\* cited by examiner

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: 341F specific 16S rRNA primers
<220> FEATURE:
<221> NAME/KEY: misc_feature
<222> LOCATION: 9
<223> OTHER INFORMATION: /note="Any nucleotide"

<400> SEQUENCE: 1
cctacgggng gcwgcag                                                         17

<210> SEQ ID NO 2
<211> LENGTH: 21
<212> TYPE: DNA
<213> ORGANISM: Artificial Sequence
<220> FEATURE:
<223> OTHER INFORMATION: 805R specific 16S rRNA primers

<400> SEQUENCE: 2
gactachvgg gtatctaatc c                                                    21
```

THERAPEUTIC USES OF *LACTOBACILLUS PLANTARUM*

CROSS-REFERENCE TO RELATED APPLICATIONS

This application is a U.S. national stage filing, under 35 U.S.C. § 371(c), of International Application No. PCT/EP2018/066152, filed on Jun. 18, 2018, which claims priority to United Kingdom Patent Application No. 1709763.5, filed on Jun. 19, 2017. The entire contents of each of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Dec. 10, 2019, is named 127275-00602_SL.TXT and is 650 bytes in size.

The present invention relates to the use of one or more *Lactobacillus plantarum* strains for increasing the numbers of *Oscillospira* spp. in a subject. Preferably, the numbers of *Oscillospira* spp. are increased for the treatment and/or prophylaxis of a dysbiosis of *Oscillospira* spp in the subject.

BACKGROUND

"Dysbiosis" is a term for a deleterious imbalance or disturbance in the normally diverse microbiota (microbial population) of the gastrointestinal tract (GI). It is known that dysbiosis of the microbiota can lead to a wide variety of deleterious conditions and/or diseases.

Dysbiosis of *Oscillospira* spp., involves decreased levels of *Oscillospira* spp., and is associated with several undesirable conditions, disorders, syndromes and/or diseases, including gastrointestinal disorders, metabolic disorders and/or inflammatory disorders or diseases, such as obesity, high BMI (Tims et al., ISME J. (April 2013); 7(4): 707-717. doi:10.1038/ismej.2012.146.Epub 2012 Nov. 29) and type 2 diabetes; autism and pervasive development disorder (De Angelis et al., (2013) PLOS ONE 8(10):e76993); flatulence (Manichanh et al., *Gut* (2014); 63:401-408); intestinal permeability (Hamilton et al., *AM J. Physiology* (2015); 308 (10): G840-G851; and Lam et al., (2012) PLOS ONE 7(3):e34233); Irritable Bowel Syndrome (IBS); and other inflammatory-related disorders, such as Inflammatory Bowel Disease (IBD) including Crohn's disease (Kaakoush et al., *J. Clinical Microbiology* (2012); 50(10):3258-3266), and/or ulcerative colitis; childhood metabolic disease and/or atopic disease; atherosclerosis; non-alcoholic fatty liver disease; dyslipidemia; and travellers' diarrhoea.

Tun et al., *Microbiome* (2017) 5:40 investigated measures for reducing the risk to health of overweight (obesity) and allergic disease. They showed that increased abundance of *Oscillospira* is caused by pre- and/or post-natal exposure to furry pets. They also noted that increased abundance of *Oscillospira* is associated with leanness or lower body mass index (BMI) in both infants and adults. Thus, increased *Oscillospira* could be the mechanism by which exposure to furry pets reduced the risk for childhood metabolic and/or atopic disease. Conversely, they noted that decreasing abundance of *Oscillospira* with obesity has been reported, in three different geographical regions, despite substantial differences in gut microbial composition.

Atherosclerosis is the major cause of myocardial infarction and stroke, which is the leading cause of death worldwide. Atherosclerosis is a chronic inflammatory disease of the arteries.

Chan et al., *BMC Microbiology* (2016) 16:264 studied high fat diet-induced atherosclerosis in mice and found that reduced *Oscillospira* abundance was associated with a significant adverse atherogenic profile, especially atherosclerotic plaque size and increased plasma levels of adipocyte-fatty acid binding protein and cholesterol. They also concluded that *Oscillospira* are most likely protective against atherosclerosis.

According to Tun et al., Microbiome (2017)5:40, the health-promoting effects of *Oscillospira* are not fully understood, but they are thought to produce butyrate by relying on fermentation products secreted by other bacterial species or on sugars liberated from host mucins.

Butyrate appears to be an important signalling molecule with other potential health benefits, including metabolic health. Acetate, propionate and butyrate are the three most abundant short chain fatty acids (SCFA) detected in the colon.

Butyrate is produced in the human intestine by certain commensal bacteria. At the intestinal level, butyrate plays a regulatory role on the transepithelial fluid transport, ameliorates mucosal inflammation and oxidative status, reinforces the epithelial defense barrier, and modulates visceral sensitivity and intestinal motility (Canani et al., *World J. Gastroenterol* (2011, March 28); 17(12):1519-1528). In addition, a growing number of studies have stressed the role of butyrate in the prevention and inhibition of colorectal cancer. The anti-inflammatory effect of butyrate may depend on the inhibition of proinflammatory macrophages and dendritic cells and the promotion of regulatory T cell generation (Arpaia et al., *Nature* (19/26 Dec. 2013) vol 504:451-455; Chang et al., *P.N.A.S* (Feb. 11, 2014) vol 111(6):2247-2252; and Singh et al., *Immunity* (Jan. 16, 2014); 40(1):128-139).

At the systemic level, butyrate exerts potentially useful effects on many conditions, including hemoglobinopathies, genetic metabolic diseases, hypercholesterolemia, insulin resistance, and ischemic stroke (Canani et al., *World J. Gastroenterol* (2011, March 28); 17(12):1519-1528).

Butyrate-producers are in lower abundance in people with metabolic disease, such as overweight, metabolic syndrome, insulin resistance, type II diabetes and dyslipidemia. Butyrate increases GLP-1 in L-cells, and may this play an active role in the control of blood glucose and help prediabetic subjects maintain normal blood glucose concentration/reduce post-prandial glycemic responses. (Yadav et al., *J. Biol. Chem* (Aug. 30, 2013); vol 288 (35):25088-25097; Qin et al., *Nature* (Oct. 4, 2012); vol 490:55-60; Karlsson et al., *Nature* (Jun. 6, 2013); vol 498:99-103; and Vrieze et al., *Gastroenterology* (2012); 143:913-916).

Butyrate-producing probiotic bacteria (*Clostridium butyricum* Miyairi 588) have been shown to reduce choline-deficient/L-amino acid-defined-diet-induced hepatic lipid deposition (non-alcoholic fatty liver disease) in rodents and significantly improved the triglyceride content, insulin resistance, serum endotoxin levels, and hepatic inflammatory indexes (Endo et al., PLOS ONE (May 2013); vol 8(5): e63388. doi:10.1371/journal.pone.0063388).

Krokowicz et al., *Travel Med. Infect. Dis* (March-April, 2014); 12(2):183-8 showed that administration of sodium butyrate and short-chain fatty acids decreased the occurrence of travellers' diarrhoea and may constitute a new method of travellers' diarrhoea prevention. Since increasing *Oscillospira* spp. numbers in accordance with the present invention can be expected to increase butyrate production, the methods uses and kits of the present invention may also find utility in the prevention and/or treatment of travellers' diarrhoea.

Hence, butyrate-producing bacteria have the potential to treat or prevent metabolic disease and/or inflammatory conditions through several different mechanisms of action (Brahe et al., *Int. Ass. For the Study of Obesity* (2013):1-9. doi:10.1111/obr.12068).

Hence, there is a need to increase levels of *Oscillospira* spp. in a subject to obtain and preferably maintain the beneficial health benefits associated therewith. In particular, there is a need to provide materials and methods for use in the treatment and/or prophylaxis of a dysbiosis of *Oscillospira* spp. However, a particular problem in developing effective treatments is that *Oscillospira* is an anaerobic bacterial genus from Clostridial cluster IV that has resisted cultivation for over a century since the first time it was observed (see Gophna et al., *Environmental Microbiology* (2017) 19(3), 835-841). Accordingly, it is not possible to culture, prepare and administer *Oscillospira* spp. to a subject in order to increase their abundance.

SUMMARY OF THE INVENTION

According to a first aspect, the invention provides a method for increasing the numbers of *Oscillospira* spp. in a subject comprising administering at least one strain of *Lactobacillus plantarum* to the subject.

Preferably, the method is for the treatment and/or prophylaxis of a dysbiosis of *Oscillospira* spp.

In a second aspect, the invention provides the use of at least one strain of *Lactobacillus plantarum* for increasing the numbers of *Oscillospira* spp. in a subject. Preferably, the use is for the treatment and/or prophylaxis of a dysbiosis of *Oscillospira* spp. in a subject.

In a third aspect, the invention provides at least one strain of *Lactobacillus plantarum* for use in the manufacture of a composition for increasing the numbers of *Oscillospira* spp. in a subject. Preferably, the use is in the treatment and/or prophylaxis of a dysbiosis of *Oscillospira* spp. in the subject.

The dysbiosis of *Oscillospira* spp. is reduced numbers of *Oscillospira* spp. and the treatment and/or prophylaxis with at least one strain of *Lactobacillus plantarum* according to the invention is effective to increase and preferably maintain increased numbers of *Oscillospira* spp. in a subject compared to *Oscillospira* spp. numbers without treatment.

By "increased numbers of *Oscillospira* spp." we include the meaning that the total number of *Oscillospira* bacteria of any and all *Oscillospira* species is increased in the subject, or a relevant sample therefrom.

DETAILED DESCRIPTION OF THE INVENTION

In the description of the invention various embodiments and/or individual components are disclosed. As will be apparent to the ordinarily skilled practitioner, all combinations of such embodiments and components taught in the disclosure are possible and can result in preferred embodiments of the present invention.

Any percentages and ratios are calculated by weight unless otherwise indicated. All percentages, parts and ratios are calculated based on the total composition unless otherwise indicated.

Referenced herein may be trade names for components including various ingredients utilized in the present invention. However, the inventors do not intend to be limited by materials under a certain trade name. Equivalent materials (eg those obtained from a different source under a different name or reference number) to those referenced by trade name may be substituted and used in the embodiments of the invention described herein.

*Lactobacillus plantarum*

The at least one *Lactobacillus plantarum* strain for use according to the invention may be any viable and/or dead *Lactobacillus plantarum* strain. Preferably, the strain is a probiotic, that is, a viable strain which, upon administration, confers a health benefit to a recipient mammal, preferably a human. The composition may comprise a single species or strain of a probiotic bacterium, or it may comprise a combination of one or more species or strains.

Particularly preferred probiotic *Lactobacillus plantarum* strains for use in the invention are selected from one or more of *Lactobacillus plantarum* 299v (DSM 9843, Deposited on 16 Mar. 1995); *Lactobacillus plantarum* 299 (DSM 6595, Deposited on Feb. 7, 1991); *Lactobacillus plantarum* HEAL 9 (DSM 15312, Deposited on 27 Nov. 2002); *Lactobacillus plantarum* HEAL 19 (DSM 15313, Deposited on 27 Nov. 2002); *Lactobacillus plantarum* HEAL 99 (DSM 15316, Deposited on 27 Nov. 2002); and *Lactobacillus plantarum* Gos 42 (DSM 32131, Deposited on Feb. 9, 2015) which have all been deposited by Probi AB of Sölvegatan 41 A, SE-223 701 Lund, Sweden at the depository DSMZ of Inhoffenstrasse 7B, 38124 Braunschweig, Germany in accordance with the provisions of the Budapest Treaty.

Other preferred probiotic *Lactobacillus plantarum* strains may be selected from one or more of *Lactobacillus plantarum* LB3e (DSM 17852 and *Lactobacillus plantarum* LB7c (DSM 17853, both deposited on Jun. 1, 2006 by ProBac AB of Box 3049, Se-903 02 Umeå, Sweden); and *Lactobacillus plantarum* LB931 (DSM 11918, deposited on Sep. 1, 1998 by Essum AB (www.essum.se) of Nygatan 74, SE-903 02 Umeå. Sweden). The three strains were all deposited at DSMZ of Inhoffenstrasse 7B, 38124 Braunschweig, Germany.

The most preferred strain for use according to the invention is *Lactobacillus plantarum* 299v (DSM 9843).

*Lactobacillus plantarum* 299 (DSM 6595) was deposited on 2 Jul. 1991 at DSM-DEUTSCHE SAMMLUNG VON MIKROORGANISMEN UND ZELLKULTUREN GmbH in the name of Probi.

*Lactobacillus plantarum* 299v (DSM 9843) was deposited on 16 Mar. 1995 at DSM-DEUTSCHE SAMMLUNG VON MIKROORGANISMEN UND ZELLKULTUREN GmbH, Mascheroder Weg 1b, D-38124 Braunschweig, Germany, by Probi AB.

*Lactobacillus plantarum* HEAL 9 (DSM 15312), *Lactobacillus plantarum* HEAL 19 (DSM 15313), and *Lactobacillus plantarum* HEAL 99 (DSM 15316) were deposited on 27 Nov. 2002 at DSMZ-DEUTSCHE SAMMLUNG VON MIKROORGANISMEN UND ZELLKULTUREN GmbH, Mascheroder Weg 1b, D-38124 Braunschweig, Germany, by Probi AB.

*Lactobacillus plantarum* GOS42 (DSM 32131) was deposited on 2 Sep. 2015 at Leibniz Institute DSMZ-German Collection of Microorganisms and Cell Cultures, Inhoffenstr. 7 B, D-38124 Braunschweig, Germany by Probi AB.

*Lactobacillus plantarum* LB3e (DSM 17852) and *Lactobacillus plantarum* LB7c (DSM 17853) were deposited on 6 Jan. 2006 at DSMZ-DEUTSCHE SAMMLUNG VON MIKROORGANISMEN UND ZELLKULTUREN GmbH, Mascheroder Weg 1b, D-38124 Braunschweig, Germany, by Probac AB. All rights and duties in connection with deposits DSM 17852 and DSM 17853 were given to and accepted by Probi AB, which is now the depositor of said strains.

*Lactobacillus plantarum* LB931 (DSM 11918) was deposited on 9 Jan. 1998 at DSMZ-DEUTSCHE SAMMLUNG VON MIKROORGANISMEN UND ZELLKULTUREN GmbH, Mascheroder Weg 1b, D-38124 Braunschweig, Germany, by Essum AB, and which was made available to the public by disclosure in granted patent EP1060240.

The viability of the probiotic bacteria may be confirmed by plating the bacteria on a suitable medium (e.g. solidified agar in a standard sized Petri dish) and counting the number of colonies formed. The measure, colony forming unit (or CFU), is used to quantify the amount of viable (live) bacteria in the composition.

Thus, the initial colony forming units (CFU) and the continued stability and viability of the composition partly depend on the amount of moisture in the composition. As described herein, the composition is packaged and stored in containers (preferably sealed container) in order to provide oxygen and moisture barrier in order to protect the integrity of the probiotic bacteria in the composition.

The colony forming units (CFU) referred to in the context of the composition of the present invention are CFU in a single dose after the preparation of the composition.

Effective Amounts of *Lactobacillus plantarum*

Preferably, at least one strain of *Lactobacillus plantarum* bacteria are present in the compositions of the invention at a CFU per dose of from $10^3$-$10^{12}$ CFU/dose to $10^8$-$10^{11}$ CFU/dose, most preferably $10^{10}$ CFU/dose.

*Lactobacillus*-Containing Compositions

The *Lactobacillus*-containing compositions of the invention may be provided in a variety of single and/or multi-dose formulations, including capsules, tablets and powders. Preferably, the compositions of the invention are adapted for oral administration to a subject.

Compositions and Formulations

The probiotic strains of the invention are preferably freeze-dried.

The probiotic strains of the invention may be provided together with a suitable carrier, diluent or excipient as a solid or liquid formulation, which may be a pharmaceutical formulation in on embodiment.

Examples of a suitable liquid carrier include water and other aqueous solvents.

Examples of a suitable solid carrier include maltodextrin, inulin, potato starch, corn starch or other vegetable starch, microcrystalline cellulose (MCC), and sugar alcohols.

The composition may be a dry fermented or non-fermented composition. In the case of a dry non-fermented composition, fermentation takes place in the gastrointestinal tract after ingestion of the composition by a subject.

In use, the probiotic strain(s) of the invention may be mixed with a liquid or solid carrier before administration to a subject. For example, the subject may mix the strain(s) with a carrier consisting of water or some other aqueous solvent, or a drink prior to intake. Similarly, the probiotic strains may be mixed with a carrier consisting of one or more foods. Preferred foods are gluten free products such as fermented or non-fermented dairy products such as yoghurts, fruit juices; beverages, soups, plant based foods such as soy products, dry food bars, baby food, infant nutrition, infant formula, breast milk replacements from birth.

Infant or baby formula milk is a particularly preferred carrier for the probiotic of *Lactobacilli* strain(s) of the invention. It may be in a dry powder form for mixing with water before feeding it to babies as a ready-to-feed liquid form. It is normally made from cows' milk and contains whey and casein protein.

The probiotic strain(s) of the invention may also be provided in a composition together with one or more ingredients of known dietary supplements, for example, micronutrients such as vitamins and minerals.

Packaging

The compositions of the present invention are typically filled in a sealed container, which provides an oxygen and moisture barrier in order to protect and maintain the viability of any live bacteria in the composition.

Preferably the composition is packaged in sealed aluminium foil sticks, where each stick comprises one dose of the composition, i.e. one dose of the probiotic bacteria.

Methods of Administration and Use

The *Lactobacillus plantarum*-containing compositions of the invention described herein are preferably orally administered, although other routes including rectal administration may be contemplated.

As used herein, the term "orally administering" with respect to the subject means that the mammal ingests or a human is directed to administer, or does administer, to oneself (or another human or other animal) one or more of the compositions herein. Where the human is directed to administer the composition, such direction can be that which instructs and/or informs the human that use of the composition may and/or will provide the referenced benefit, for example, alleviation of one or more symptoms associated with a disease or condition. For example, such direction may be oral direction (eg through oral instruction from, for example, a physician, pharmacist, nurse, or other health professional), radio or television media (ie advertisement), or written direction (eg through written direction from, for example, a health professional (eg scripts), sales professional or organization (eg through, for example, marketing brochures, pamphlets, written media (eg internet, electronic mail, or other computer-related media), and/or packaging associated with the composition (eg a label present on a container holding the composition). As used herein, "written" means through words, pictures, symbols, and/or other visible descriptors. Such information need not utilize the actual words used herein, for example, "human", or "treatment", but rather use of words, pictures, symbols, and the like conveying the same or similar meaning are contemplated within the scope of this invention.

Administration may be on an as-needed or as-desired basis in order to increase and preferably maintain increased numbers of *Oscillospira* spp., for example, once-monthly, once-weekly, or daily, including multiple times daily, to arrive at a total daily dose or amount of probiotic bacteria, whether administered every day, one day per week, one day per month, or on a given day as needed. The amount of composition utilized may be dependent on a variety of factors, including the health status of the subject mammal, age, gender, or other like factors of ordinary consideration.

Preferably, the subjected treated in accordance with the invention is mammalian, most preferably human, bovine, canine or feline; or avian, most preferably one or more species of poultry such as chickens or turkeys.

In a preferred embodiment the subject is a human selected from: a male or female infant between 0-6 months old; a male or female child from 6 months to 16 years old, especially 6 months-6 years old; and a male or female adult.

The male or female adult may be from 16-65, or more than 65 years old. The human female adult may be of child-bearing age or be post-menopausal.

Detection and Enumeration of *Oscillospira* Spp.

Preferably, numbers of *Oscillospira* spp. are detected in relevant biological samples. For example, samples can be taken from the rumen (fluid or whole rumen content samples) of herbivore mammals such as domestic cattle or sheep; faecal samples and/or samples can also be taken from appropriate regions of the GI tract of humans.

Suitable molecular techniques for detecting and enumerating *Oscillospira* spp. are described in Mackie et al, *Applied and Environmental Microbiology*, November 2003, p 6808-6815 and involve the use of PCR primers based on *Oscillospira*-specific 16S ribosomal RNA gene sequences.

In particular, Mackie et al, (2003) describe PCR and PCR-denaturing gradient gel electrophoresis (DGGE) procedures for the detection of *Oscillospira* spp. They used the techniques to determine the occurrence of this bacterium in different ruminants including cattle, sheep and reindeer.

Klindworth et al., *Nucleic Acids Research* vol. 41, No. 1 (published online 28 Aug. 2012) evaluated general 16S ribosomal RNA gene PCR primers and provide guidelines for selecting suitable primer pairs for studying microbial levels and diversity for classical and next-generation sequencing-based studies.

The level of *Oscillospira* spp. in said test sample can be compared to a level of said *Oscillospira* spp. in a control sample. The control sample may advantageously be derived from a healthy subject or from a pool of samples from healthy subjects, and is preferably treated in the same way as is the test sample. Thus, preferably the control sample is sampled in the same way as is the test sample, if applicable, nucleic acid is isolated in the same way as is the test sample, and, if applicable, hybridization or quantitative amplification is performed under the same conditions to allow a fair comparison of the test sample and control sample. It is not necessary to determine the level of *Oscillospira* spp. in a control sample each time a test sample is measured; once the level is reliably determined in a control sample, the level values may be stored, e.g., in a computer, and used for the comparative purposes.

Other suitable methods of enumerating *Oscillospira* spp. in a subject are disclosed in US 2012/0238468, the disclosure of which concerning determining and comparing the levels of *Oscillospira* spp. in samples from healthy and diseased subjects is incorporated herein by reference.

The level of said *Oscillospira* spp. in a test sample can be compared to the same bacteria in a control sample. A decreased level of *Oscillospira* spp. is related to a diagnosis that the test sample is from a subject suffering from a dysbiosis of *Oscillospira* spp., such as one associated with Irritable Bowel Syndrome.

As used herein, the level of *Oscillospira* bacteria in a test sample is increased when it is significantly higher than the level of said *Oscillospira* bacteria in a control sample. It is also considered increased when the level of *Oscillospira* bacteria in the test sample is at least 1-fold, 2-fold, 5-fold, 10-fold, 100-fold, 1000-fold or higher than the numbers of *Oscillospira* bacteria in the control sample.

As used herein, the numbers or level of *Oscillospira* bacteria in a test sample is decreased when it is significantly lower than the level of said *Oscillospira* bacteria in a control sample. It is also considered decreased when the level of *Oscillospira* bacteria in the test sample is at least 1-fold, 2-fold, 5-fold, 10-fold, 100-fold or 1000-fold lower than the level of *Oscillospira* in the control sample.

The levels of the nucleic acid sequences in a test sample may be subjected to statistical and/or bioinformatical analysis to obtain analyzed data; and the analyzed data of said test sample may be compared to analyzed data from a control sample, to provide a diagnosis of whether the test sample is from a subject suffering from a dysbiosis of *Oscillospira* spp. and any related disorder such as Irritable Bowel Syndrome. For example, hybridization patterns on a micro-array comprising the nucleic acid sequences may be processed using statistical and/or bioinformatical analysis such as Principal Component Analysis (PCA) and/or Redundancy Analysis (RDA). The analyzed data may then be compared to analyzed data from a control sample which has been subject to the same statistical and/or bioinformatical analysis.

Significance Analysis of Microarrays (SAM) can be used in comparing the levels of said three or more nucleic acid sequence from said test sample with the levels of nucleic acid sequence from a control sample. The person skilled in the art is capable of performing SAM analysis. SAM analysis is described in detail by Tusher et al. (Proc Natl Acad Sci USA, 2001, vol 98:5116-5121), which is herein incorporated by reference.

Prediction Analysis of Microarray (PAM) can be used in comparing the levels of said nucleic acid sequence from said test sample with the levels of nucleic acid sequence from a control sample. The person skilled in the art is capable of performing PAM analysis. PAM analysis is described in detail by Tibshirani et al., (*Proc Nat Acad Sci USA,* 2002, vol 99:6567-6572), which is herein incorporated by reference.

Redundancy Analysis (RDA) can be used in comparing the levels of nucleic acid sequence from said test sample with the levels of nucleic acid sequence from a control sample. The person skilled in the art is capable of performing RDA analysis. RDA analysis is described in detail by Leps and Smilauer (2003. Cambridge University Press: Multivariate analysis of ecological 780 data using CANOCO), which is herein incorporated by reference.

EXAMPLES

Figure 2:
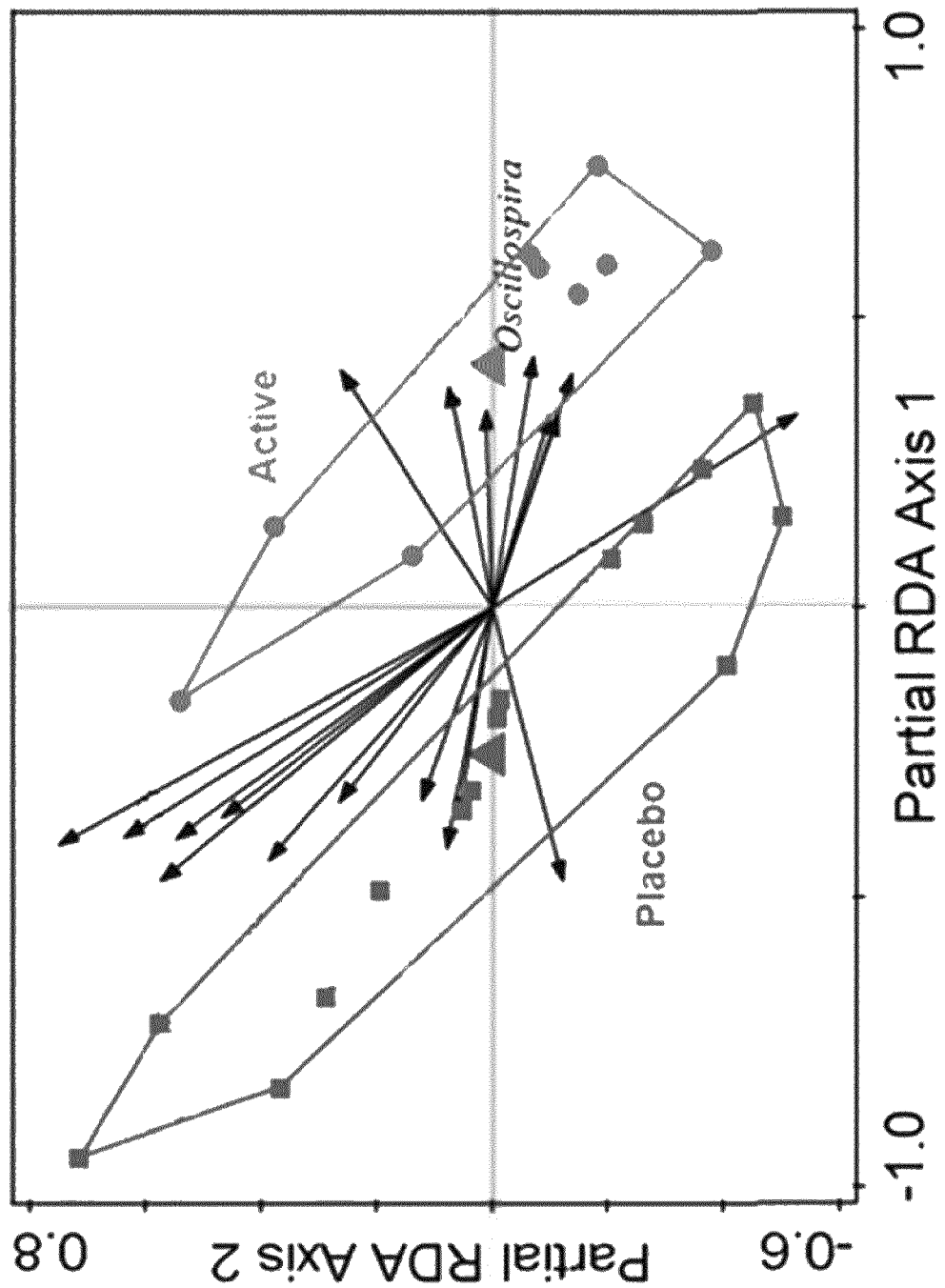

The following non-limiting examples embody certain aspects of the invention and are described with reference to the accompanying figures in which:

FIGS. 1 and 2 show the results of Redundancy Analysis (RDA).

RDA is a multivariable analysis technique that identifies the difference between sample groups that can be explained by a set of variables. In the RDAs in FIGS. 1 and 2, different sample properties (e.g. treatment group; treatment responders, etc.) are explained by microbiota compositions at the genus level.

In the RDA FIGS. 1 and 2 every dot is a sample. Black arrows represent genera and point in the direct of samples in which a genus is highly abundant. For discreet classes, the colours and shape of sample symbols indicate sample class. The coloured polygons ("envelopes") enclose all samples in a class. Large triangles are centroids ("average sample" of a class).

FIG. 1 Redundancy Analysis (RDA) of 93 samples showed that 4 weeks of treatment with *Lactobacillus plantarum* resulted in a different microbiota composition in the (active=circle symbol) group that received the *Lactobacillus plantarum* treatment ($10^{10}$ CFU once daily capsule containing freeze-dried *Lactobacillus plantarum* bacteria and excipient powder) vs. the placebo group (=square symbol), with the active group showing increased numbers of *Oscillospira* spp.

Figure 3A:
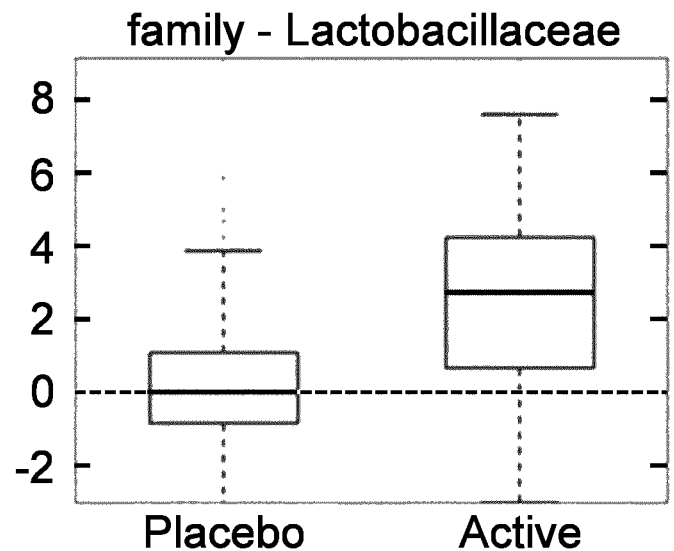
Figure 3B:
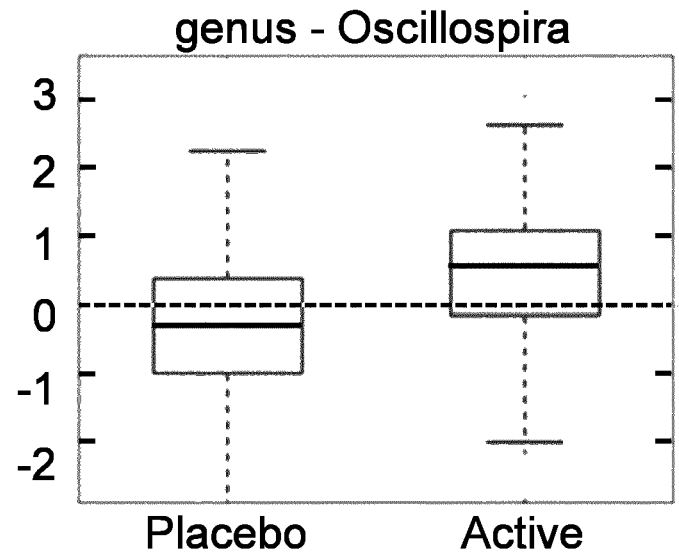
Figure 3C:
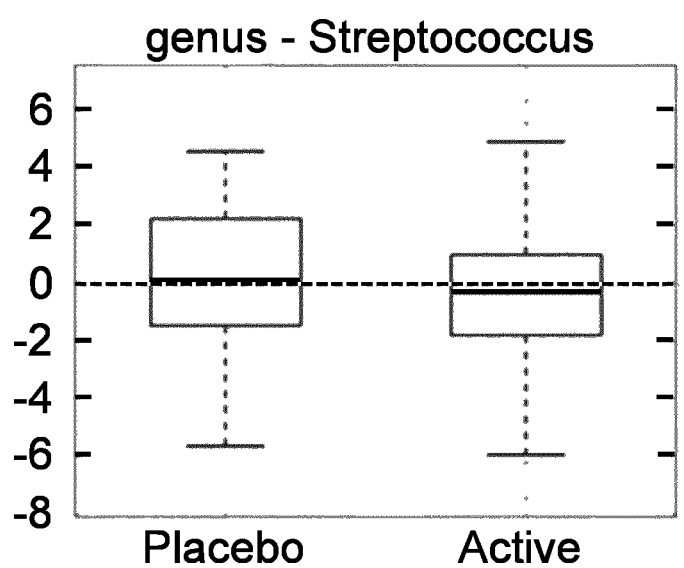

FIG. 2 Redundancy Analysis of 24 samples from individuals who were determined to be "abdominal pain responders according to the EMA guideline" (i.e. felt ≥30% better than their mean baseline value for ≥50% of the treatment period). *Oscillospira* spp. levels are higher in the group that received the *Lactobacillus plantarum* treatment (active) than in the group that received placebo;

FIG. 3 shows the difference between "active" and "placebo" on a per-subject basis. The question the data addresses is: for a specific taxon, is the change in abundance going from "before" to "after" treatment different for subjects in the "active" and "placebo" groups? The vertical axis: 2 log (after/before) where an increase on the vertical axis signifies an increase in abundance with time. A selective effect is revealed by the analysis: There is only a significant difference in the first two boxplots: 3(a) *Lactobacillaceae* reflecting the *Lactobacillus plantarum* administered to subjects; and 3(b) *Oscillospira* spp. *Streptococcus* levels (3(c)) are unaffected by the treatment with *Lactobacillus plantarum*.

Example 1

Clinical trial: The study was a randomised, placebo-controlled, double-blind, parallel, intervention study with voluntary IBS out-patients with IBS according to Rome III criteria. After a screening visit and a 2 week run-in period patients with abdominal pain score between 3-6 on a 0-10 point Likert scale with a frequency of at least two days a week were randomised to receive either *Lactobacillus plantarum* 299v ($10^{10}$ CFU/capsule) or placebo capsules one capsule per day for 4 weeks. A faecal sample was taken at the end of the run-in period and at the end of the intervention period. A food and physical activity questionnaire was filled in at the randomisation visit and at the last visit.

16S rRNA gene profiling: Illumina 16S rRNA gene amplicon libraries were generated and sequenced. In short, barcoded amplicons from the V3-V4 region of 16S rRNA genes were generated using a 2-step PCR. 10-25 ng genomic (g) DNA was used as template for the first PCR with a total volume of 50 ul using the 341F (5'-CCTACGGG-NGGCWGCAG-3', SEQ ID NO: 1) and the 805R (5'-GACTACHVGGGTATCTAATCC-3', SEQ ID NO: 2) specific 16S rRNA primers appended with Illumina adaptor sequences. PCR products were purified and the size of the PCR products were checked on a Bioanalyzer (Agilent) and quantified by fluorometric analysis. Purified PCR products were used for the 2nd PCR in combination with sample-specific barcoded primers (Nextera XT index kit, Illumina). Subsequently, PCR products were purified, checked on a Bioanalyzer (Agilent) and quantified, followed by multiplexing, clustering, and sequencing on an Illumina MiSeq with the paired-end (2×) 300 bp protocol and indexing. The sequencing run was analyzed with the Illumina CASAVA pipeline (v1.8.3) with demultiplexing based on sample-specific barcodes. The raw sequencing data produced was processed removing the sequence reads of too low quality (only "passing filter" reads were selected) and discarding reads containing adaptor sequences or PhiX control with an in-house filtering protocol. A quality assessment on the remaining reads was performed using the FASTQC quality control tool version 0.10.0.

Bioinformatics: Microbiota composition analysis: microbiota composition was determined using a modified Qiime 1.8 workflow. Sample clustering was done with the "pick_openreference_otus" workflow script (97% identity) against the 13.8 version of the GreenGenes database using usearch as clustering methods. Reference-based chimera removal was done with uchime.

Multivariate statistics: redundancy analysis (RDA) was done with Canoco 5.0.

Univariate statistics were done in Scientific Python, using non-parametric tests (Mann-Whitney and Kruskal Wallis for unpaired data, Wilcoxon signed rank for paired data).

Results

Both fiber and Bristol Stool Scale (BSS) Score were shown to be confounders and were corrected for in the analyses. Feces samples without a corresponding BSS Score for that day were therefore removed from the analysis.

A redundancy analysis (RDA) revealed a trend towards a differential microbiota composition in the placebo group vs the active group at endpoint. The univariate analysis showed that the abundance of the genus *Oscillospira* was significantly higher in the active group at endpoint after correction for multiple testing.

According to the European Medicines Agency (EMA) Guidelines on the evaluation of medical products for the treatment of irritable bowel syndrome (IBS) dated 25 Sep. 2014, an IBS patient is classified as a responder for abdominal pain if for at least 50% of the treatment time they exhibit an abdominal pain score which has improved at least 30% compared to their baseline score.

FIG. 1 analysis of 93 samples showed that after weeks of treatment with *Lactobacillus plantarum* ($10^{10}$ CFU per day) resulted in a different microbiota composition in the group that received the *Lactobacillus plantarum* treatment (active) vs. the placebo group, with the active group showing increased numbers of *Oscillospira* spp.

FIG. 2 analysis of 24 sample from responders for abdominal pain according to the EMA guidelines (i.e. they felt ≥30% better than their mean baseline value for ≥50% of the treatment period). *Oscillospira* spp. levels are higher in the group that received the *Lactobacillus plantarum* treatment (active) than in the group that received placebo;

FIG. 3 shows the difference between "active" and "placebo" on a per-subject basis, pairing "before" with "after" data. The question the data addresses is: for a specific taxon, is the change in abundance going from "before" to "after" treatment different for subjects in the "active" and "placebo" groups? A selective effect is revealed by the analysis: There is only a significant difference after correction for multiple testing in the first two boxplots: 3(a) *Lactobacillaceae* reflecting the *Lactobacillus plantarum* administered to subjects; and 3(b) *Oscillospira* spp. *Streptococcus* levels (3(c)) are unaffected by the treatment with *Lactobacillus plantarum*.

Overall, the present results show that treatment with *Lactobacillus plantarum* is effective to increase the numbers of *Oscillospira* spp. in a subject. Further, the results show that increased numbers of *Oscillospira* are associated with a pain response benefit in IBS patients treated with *Lactobacillus plantarum*. Hence, the invention should have application in the treatment and/or prophylaxis of a wide range of other disorders and diseases that have been associated with low levels of *Oscillospira*, which is a predicted butyrate-producer, and/or with disorders and diseases that have been associated with a low abundance of butyrate-producers.

The invention claimed is:

1. A method for increasing the numbers of *Oscillospira* spp. in a subject in need thereof, the method comprising administering at least one strain of *Lactobacillus plantarum* to the subject to increase the numbers of *Oscillospira* spp. in the subject, wherein the method treats a dysbiosis of *Oscillospira* spp., and wherein said dysbiosis of *Oscillospira* spp. is associated with Irritable Bowel Syndrome (IBS).

2. The method as claimed in claim 1, further comprising: prior to administration, instructing the subject to take or receive the at least one strain of *Lactobacillus plantarum* in order to increase the subject's numbers of *Oscillospira* spp.

3. The method as claimed in claim 1, wherein the method is effective to maintain an increase in *Oscillospira* spp. numbers in the subject.

4. The method as claimed in claim 1, wherein the at least one strain of *Lactobacillus plantarum* is administered orally.

5. The method as claimed in claim 1, wherein the at least one strain of *Lactobacillus plantarum* is administered in an amount of from $10^8$-$10^{11}$ CFU per daily dose, preferably $10^{10}$ CFU per daily dose.

6. The method as claimed in claim 1, wherein the at least one strain of *Lactobacillus plantarum* is selected from one or more of: *Lactobacillus plantarum* 299v (DSM 9843); *Lactobacillus plantarum* 299 (DSM 6595); *Lactobacillus plantarum* HEAL 9 (DSM 15312); *Lactobacillus plantarum* HEAL 19 (DSM 15313); *Lactobacillus plantarum* HEAL 99 (DSM 15316); and *Lactobacillus plantarum* Gos 42 (DSM 32131); *Lactobacillus plantarum* LB3e (DSM 17852); *Lactobacillus plantarum* LB7c (DSM 17853); and/or *Lactobacillus plantarum* LB931 (DSM 11918).

7. The method as claimed in claim 1, wherein the at least one strain of *Lactobacillus plantarum* is *Lactobacillus plantarum* 299v (DSM 9843).

8. The method as claimed in claim 1, wherein the at least one strain of *Lactobacillus plantarum* is provided in a composition in combination with an excipient or carrier material.

9. The method as claimed in claim 8 wherein the excipient is a pharmaceutically acceptable excipient.

10. The method as claimed in claim 8, wherein the carrier material is a human food material and/or an animal food material.

11. The method as claimed in claim 1, wherein the at least one strain of *Lactobacillus plantarum* is provided as a composition in combination with a micronutrient, such as a mineral and/or vitamin.

12. The method as claimed in claim 8, wherein the composition is adapted for oral administration.

13. The method as claimed in claim 1, further comprising: prior to administration, instructing the subject to take or receive the at least one strain of *Lactobacillus plantarum* in order to increase the subject's numbers of *Oscillospira* spp.

* * * * *